(12) United States Patent
Curry et al.

(10) Patent No.: US 9,295,623 B2
(45) Date of Patent: Mar. 29, 2016

(54) METHODS OF PREVENTING THE TRANSMISSION OF COMMUNICABLE DISEASES IN LIVESTOCK

(71) Applicant: EQ Ag Solutions, Hewitt, TX (US)

(72) Inventors: Patrick J. Curry, McGregor, TX (US); Franklin Irven Diehl, Ruskin, FL (US)

(73) Assignee: EQ Ag Solutions, Hewitt, TX (US)

( * ) Notice: Subject to any disclaimer, the term of this patent is extended or adjusted under 35 U.S.C. 154(b) by 571 days.

(21) Appl. No.: 13/573,704

(22) Filed: Oct. 3, 2012

(65) Prior Publication Data

US 2013/0081576 A1    Apr. 4, 2013

Related U.S. Application Data

(60) Provisional application No. 61/542,359, filed on Oct. 3, 2011.

(51) Int. Cl.
| | |
|---|---|
| *A01K 13/00* | (2006.01) |
| *A01N 59/00* | (2006.01) |
| *C11D 3/38* | (2006.01) |
| *A61K 8/46* | (2006.01) |
| *A61Q 19/10* | (2006.01) |
| *C11D 3/48* | (2006.01) |

(52) U.S. Cl.
CPC .............. *A61K 8/463* (2013.01); *A61K 8/466* (2013.01); *A61Q 19/10* (2013.01); *A01K 13/003* (2013.01); *A01N 59/00* (2013.01); *C11D 3/48* (2013.01)

(58) Field of Classification Search
CPC ... A01N 41/04; A01N 2300/00; A01N 25/30; A01N 25/02; A01N 41/02; A01N 37/40; A01N 59/00; C11D 3/48; C11D 1/29409; A01K 13/003; A01K 27/007; A01K 13/001

USPC ............ 119/651, 652, 650; 424/405; 510/389
See application file for complete search history.

(56) References Cited

U.S. PATENT DOCUMENTS

| | | | | |
|---|---|---|---|---|
| 3,421,882 | A * | 1/1969 | Ordas ........................... | 504/307 |
| 3,933,671 | A * | 1/1976 | Heile ............................ | 510/386 |
| 4,124,520 | A * | 11/1978 | Schwalley et al. ............ | 510/386 |
| 4,198,441 | A * | 4/1980 | Young et al. ................... | 427/2.1 |
| 4,205,624 | A * | 6/1980 | Yacus ........................... | 119/174 |
| 4,252,665 | A * | 2/1981 | Casey et al. ................... | 510/386 |
| 4,544,547 | A * | 10/1985 | von Bittera et al. .......... | 424/411 |
| 4,589,994 | A * | 5/1986 | Moseman ...................... | 424/770 |
| 4,670,171 | A * | 6/1987 | Magyar ......................... | 510/189 |
| 6,004,604 | A * | 12/1999 | Thomas et al. ................ | 426/326 |
| 6,029,610 | A * | 2/2000 | Ramsey et al. ................ | 119/651 |
| 6,514,556 | B2 * | 2/2003 | Hilgren et al. ................ | 426/652 |
| 6,617,290 | B2 * | 9/2003 | Lopes ........................... | 510/111 |
| 7,060,301 | B2 * | 6/2006 | Wei et al. ....................... | 424/616 |
| 7,544,706 | B2 * | 6/2009 | Chubb et al. .................. | 514/396 |
| 2004/0043912 | A1 * | 3/2004 | Murch et al. .................. | 510/111 |
| 2009/0192231 | A1 * | 7/2009 | Lemons ........................ | 514/738 |
| 2010/0323037 | A1 * | 12/2010 | Curry et al. ................... | 424/722 |

* cited by examiner

*Primary Examiner* — Yvonne Abbott-Lewis
(74) *Attorney, Agent, or Firm* — Schwegman Lundberg & Woessner, P.A.

(57) ABSTRACT

A composition that includes ethylhexyl sulfate or a salt thereof, an alkylbenzenesulfonic acid or a salt thereof, and a carrier. The composition can be used for killing or inhibiting a microorganism or pathogen (e.g., bacteria, gram-negative bacteria, gram-positive bacteria, enteric bacteria, virus, fungus, mold, mildew or powdery mildew), located on a topical surface of an animal, located on a surface of an object that will contact a topical surface of an animal, or a combination thereof, wherein the microorganism or pathogen is associated with the transmission of communicable diseases.

19 Claims, No Drawings

METHODS OF PREVENTING THE TRANSMISSION OF COMMUNICABLE DISEASES IN LIVESTOCK

SUMMARY

The compositions described herein are effective in killing or diminishing a variety of organisms or pathogens (such as bacteria, mold, yeast, fungus and/or virus), specifically associated with communicable diseases. The compositions have been found to be food grade, readily biodegradable, environmentally friendly, non-corrosive and/or inert. The compositions are biodegradable in that they can be disposed of using normal septic or municipal sewage facilities according to local and state regulations. In addition to being safe for topical use with humans and livestock, the compositions upon topical application can either be rinsed off with water, or can safely be left unrinsed for a residual effect. The compositions are also compatible with other substances, e.g., chlorine (at recommended dilute levels), typically used in sanitizing livestock related equipment and products. The compositions also comply with the relevant Federal Rules and Regulations, e.g., 40 CFR 180.910 (EPA), 40 CFR 180.920 (EPA), 40 CFR 180.940 (EPA) and/or 21 CFR 173.315 (FDA).

The present invention provides a method of preventing or diminishing the occurrence of the transmission of a communicable disease capable of being transmitted by physical contact. The present invention also provides a method of reducing the number of microbes located upon a topical skin surface of an animal, wherein the microbes are associated with the transmission of a communicable disease. The present invention also provides a method of reducing the number of microbes located upon a surface that contacts a topical skin surface of an animal, wherein the microbes are associated with the transmission of a communicable disease. The present invention also provides a method of washing a topical skin surface of an animal. The present invention also provides a method of washing a surface that contacts a topical skin surface of an animal. The present invention also provides a method of disinfecting a topical skin surface of an animal. The present invention also provides a method of disinfecting a surface that contacts a topical skin surface of an animal.

The method includes contacting a topical skin surface of an animal, or contacting a surface that in normal use will contact a topical skin surface of an animal, with an effective amount of a composition that includes: (a) ethylhexyl sulfate of the formula

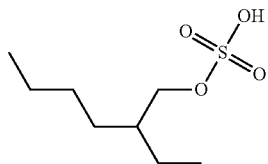

or a salt thereof;
(b) an alkylbenzenesulfonic acid of the formula

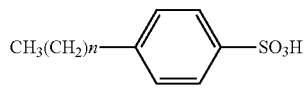

or a salt thereof, wherein n is about 5 to about 20; and
(c) an acceptable carrier.

In specific embodiments, the amount of composition is effective to prevent or diminishing the occurrence of the transmission of a communicable disease.

DETAILED DESCRIPTION

The compositions described herein are effective against a variety of organisms, such as bacteria, mold, yeast, fungus and/or virus. Additionally, the compositions described herein rapidly (e.g., in 30 seconds or less) kill those pathogens associated with the transmission of communicable diseases on, for example, surfaces that routinely come into contact with humans and livestock. The presently disclosed subject matter includes the use of a composition that includes ethylhexyl sulfate or a salt thereof, an alkylbenzenesulfonic acid or a salt thereof, and a carrier. The ethylhexyl sulfate, or salt thereof, and the alkylbenzenesulfonic acid, or salt thereof, are present in a weight ratio of at least about 1:2. That is, based upon a weight basis, the amount of ethylhexyl sulfate, or salt thereof is at least about a half (i.e., 50%) that of the alkylbenzenesulfonic acid, or salt thereof.

In a specific embodiment, the ethylhexyl sulfate, or salt thereof, and the alkylbenzenesulfonic acid, or salt thereof, are present in a weight ratio of least about 1:1. That is, based upon a weight basis, the amount of ethylhexyl sulfate, or salt thereof is at least about equal (i.e., 100%) that of the alkylbenzenesulfonic acid, or salt thereof.

In a more specific embodiment, the ethylhexyl sulfate, or salt thereof, and the alkylbenzenesulfonic acid, or salt thereof, are present in a weight ratio of about 1:2 to about 3:1. That is, based upon a weight basis, the amount of ethylhexyl sulfate, or salt thereof is at least a half (i.e., 50%) that of the alkylbenzenesulfonic acid, or salt thereof; and is no more than about three times (i.e., 300%) that of the alkylbenzenesulfonic acid, or salt thereof.

In a more specific embodiment, the ethylhexyl sulfate, or salt thereof, and the alkylbenzenesulfonic acid, or salt thereof, are present in a weight ratio of about 1:2 to about 2:1. That is, based upon a weight basis, the amount of ethylhexyl sulfate, or salt thereof is at least about a half (i.e., 50%) that of the alkylbenzenesulfonic acid, or salt thereof; and is no more than about two times (i.e., 200%) that of the alkylbenzenesulfonic acid, or salt thereof.

In a more specific embodiment, the ethylhexyl sulfate, or salt thereof, and the alkylbenzenesulfonic acid, or salt thereof, are present in a weight ratio of about 1:2 to about 1.5:1. That is, based upon a weight basis, the amount of ethylhexyl sulfate, or salt thereof is at least about a half (i.e., 50%) that of the alkylbenzenesulfonic acid, or salt thereof; and is no more than about one and a half times (i.e., 150%) that of the alkylbenzenesulfonic acid, or salt thereof.

Ethylhexyl sulfate refers to a compound of the formula

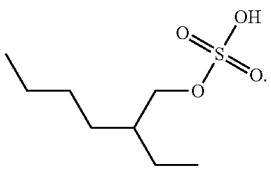

Sodium ethylhexyl sulfate, CAS Reg. No. 126-92-1, alternatively known as NAS 08 or NIAPROOF 08, is present in NIAPROOF anionic surfactant 08 in 38.5-40 wt. %. NIAPROOF anionic surfactant 08 also includes sodium chloride (1.5-2.5 wt. %) and the balance of water. NIAPROOF anionic surfactant 08 is commercially available from Niacet Corp. (Niagara Falls, N.Y.).

An alkylbenzenesulfonic acid refers to a compound of the formula

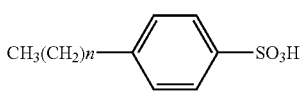

wherein n is about 5 to about 20. In specific embodiments, n will have an average value of 5, 6, 7, 8, 9, 10, 11, 12, 13, 14, 15, 16, 17, 18, 19 or 20. In further specific embodiments, n will have an average value of about 8 to about 12. In further specific embodiments, n will have an average value of about 9 to about 11. Alkylbenzenesulfonic acid ($C_{10}$-$C_{16}$), CAS Reg. No. 68584-22-5, is present in Calsoft® LAS-99 and Bio-Soft® S-101 in over 95.5%. Benzene and other aromatic derivatives are also present in Calsoft® LAS-99 and Bio-Soft® S-101 in 2%. Additionally, sulfuric acid (1.3%) is present in Calsoft® LAS-99 and Bio-Soft® S-101. Bio-Soft® S-101 is commercially available from Stepan Co. (Northfield, Ill.). Calsoft® LAS-99 is commercially available from Pilot Chemical Company (Cincinnati, Ohio).

Carrier

The composition includes a carrier. A carrier refers to a substance in which the ethylhexyl sulfate, or salt thereof, and the alkylbenzenesulfonic acid, or salt thereof, can be dissolved into or mixed with. Any suitable and effective carrier can be employed, provided the carrier is stable over the periods of time typically encountered with the manufacturing, shipping and storage of the composition. Additionally, the carrier will preferably be chemically and physically compatible with the ethylhexyl sulfate, or salt thereof, and the alkylbenzenesulfonic acid, or salt thereof.

In a specific embodiment, the carrier includes at least one of water, ethanol, triethylene glycol, ethylene glycol, glycerin, propylene glycol, triacetin, 1,3-propane diol, 2-methyl-1,3-propane diol, glycerol ricinoleate, PEG-6 caprylic/capric glycerides, caprylic/capric triglycerides, propyleneglycol dicaprylate/dicaprate, glycerol monostearate, glycerol monocaprylate, glycerol monolaurate, neopentyl alcohol, 1-hexademayol, hydroxypropyl beta-cyclodextrin, vitamin E, vitamin E acetate, deoxycholic acid, taurodeoxycholic acid, 3-[(3-cholamidopropyl)dimethylammonio]-1-propane-sulfonate, BigCHAP, cholic acid, cholesterol NF, propylene carbonate, lecithin, and salts thereof. In a more specific embodiment, the carrier includes water.

Base

In specific embodiments, the composition can optionally further include a base. The base can be an organic base or an inorganic base. The base, when present in the composition, will effectively produce one or more hydroxyl ions ($OH^-$). In a specific embodiment, the base can include at least one of a lithium ion ($Li^+$), a sodium ion ($Na^+$), a potassium ion ($K^+$), a calcium ion ($Ca^{2+}$), and a barium ion ($Ba^+$). More specifically, the base can include at least one of sodium hydroxide (NaOH) and potassium hydroxide (KOH).

The base can be present in any suitable and appropriate amount. For example, the base can be present in an amount, such that the pH of the composition is above about 6. Specifically, the base can be present in an amount, such that the pH of the composition is, e.g., about 6 to about 13. More specifically, the base can be present in an amount, such that the pH of the composition is, e.g., about 7 to about 9, or about 7 to about 8.5. Additionally, the base can be employed, e.g., not to adjust the pH above 7 (i.e., neutral pH), but to neutralize, or partially neutralize, acid present in the composition. For example, the base can be employed to neutralize, or partially neutralize the sulfurinc acid present from the Bio-Soft S-101.

The amount of base can depend, e.g., upon the amount of ethylhexyl sulfate, or salt thereof, and the alkylbenzenesulfonic acid, or salt thereof. For example, the base (e.g., sodium hydroxide, potassium hydroxide, or combination thereof) can be present in a weight ratio of less than about 1:4, relative to the ethylhexyl sulfate, or suitable salt thereof.

Sodium Chloride

The commercial product NIAPROOF 08 currently includes sodium chloride (1.5-2.5 wt. %). As such, when the current formulation of NIAPROOF 08 is employed as the source of the ethylhexyl sulfate, or salt thereof, sodium chloride will be present in the composition. Alternatively, when the current formulation of NIAPROOF 08 is not employed as the source of the ethylhexyl sulfate, or salt thereof, sodium chloride can be included within the composition, or the sodium chloride can be omitted from the composition.

When present, the sodium chloride can be present in up to about 5 wt. % of the composition, up to about 1 wt. % of the composition or up to about 0.1 wt. % of the composition.

Acid

The commercial product Bio-Soft S-101 currently includes sulfurinc acid (1.3%). As such, when the current formulation of Bio-Soft S-101 is employed as the source of the alkylbenzenesulfonic acid, or salt thereof, sulfuric acid will be present in the composition. The sulfuric acid can be present in the free acid form, or can be used to neutralize any base present in the composition. Alternatively, when the current formulation of Bio-Soft S-101 is not employed as the source of the alkylbenzenesulfonic acid, or salt thereof, sulfuric acid can be included within the composition, or the sulfuric acid can be omitted from the composition. Likewise, other suitable acids (e.g., lactic acid) can be employed in the composition.

When present, each of the acids can independently be present in up to about 5 wt. % of the composition, up to about 1 wt. % of the composition or up to about 0.1 wt. % of the composition.

Disinfectant

The composition can optionally further include a disinfectant. Additionally, the methods described herein can further include the use of a disinfectant, in combination with the composition described herein. In such a situation, the use of the disinfectant can be concurrent with the use of the composition, or can be sequential with the use of the composition.

The disinfectant can be any substance that effectively inhibits or kills a microorganism. Specific disinfectants include, e.g., chlorine dioxide, chlorine gas, or any substance that would effectively generate chlorine gas, e.g., upon contact with the composition described herein. Additional specific disinfectants include e.g., ozone ($O_3$), lactic acid, ultraviolet light, peroxides, peracetic acid (peroxyacetic acid, or PAA), potassium sorbate and lactic acid.

Formulation

The composition can be formulated into any suitable and effective formulation. Specific formulations include, e.g., creams, gels, pastes, ointments, lotions, fluid liquids liquid soaps, and aerosol sprays.

Alternatively, the composition can be physically present in a wipe. The wipe can include a flexible cloth, wherein the composition is positioned (i.e., located) on at least a portion of a surface of the flexible cloth. The flexible cloth can be manufactured from any suitable and effective materials. For example, the flexible cloth can include a non-woven fabric. Specifically, the flexible cloth can include at least one of polycellulose fibers, polyester fibers, polyurethane fibers, polyolefin fibers, polyamide fibers, cotton fibers, copolyester fibers and films. Additionally, the composition can be at least partially embedded in at least a portion of the flexible cloth.

Antibiotic Agent

The composition can optionally further include an antibiotic agent. Suitable specific antibiotic agents include, e.g., cilastatin, clavulanic acid, folinic acid, probenecid, pyridoxine, sulbactam, dapsone, ethambutol, isoniazid, pyrazinamide, rifampin, streptomycin, capreomycin, ethionamide, para aminosalicylic acid, cycloserine, ciprofloxacin, nalidixic acid, norfloxacin, ofloxacin, imipenam, meropenem, cilistatin, cefadroxil, cefazolin, cephalexin, cephalothin, cefaclor, cefamandole, cefonicid, cefoxitin, cefuroxine, cefoperazone, cefotaxime, ceftazidime, ceftazidime, ceftizoxime, ceftriaxone, moxalactam, cefepine, bacitracin, vancomycin, aztreonam, amoxicillin, clavulanic acid, benzathine, penicillin g, penicillin v, ampicillin, carbenicillin indamyl, carbenicillin, mezlocillin, piperacillin, ticarcillin, cloxacillin, dicloxacillin, floxacillin, methicillin, nafcillin, oxacillin, colistmethate, polymixin b, trimethoprim, co-trimoxazole, mafenide, sulfadiazine, sodium sulfacetamide, sulfacytine, sulfadiazine, sulfamethoxazole, sulfapyridine, sulfasalazine, sulfisoxazole, chloramphenicol, clindamycin, spectinomycin, azithromycin, clarithromycin, erythrmoycin, erythromycin estolate, spiramycin, chlortetracycline, demeclocycline, doxycycline, minocycline, oxytetracycline, amikacin, kanamycin, neomycin, streptomycin, tobramycin, nitrofurantoin, griseofulvin, potassium iodide, fluconazole, itraconazole, ketoconazole, miconazole, clotrimazole, amphotericin b, nystatin, niclosamide, nifurtimox, piperazine, praziquantel, pyrantel pamoate, thiabendazole, amodiaquine, chloroquine, hydroxychloroquine, mefloquine, primaquine, pyrimethamine, quinidine gluconate, fansidar, diloxanide furoate, melarsoprol, nifurtimox, paromomycin, pentamidine, sodium stibogluconate, suramin, metronidazole, foscarnet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, foscarnet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, and salts thereof.

The antibiotic agent can be present in the composition in any suitable and effective amount, provided the antibiotic agent affectively inhibits or kills the desired bacterium. Specific exemplary amounts include, e.g., up to about 10 wt. % of the composition, up to about 5 wt. % of the composition, or up to about 1 wt. % of the composition.

Antiviral Agent

The composition can optionally further include an antiviral agent. Suitable specific antiviral agents include, e.g., *Echinacea* (*Echinacea angustifolia, E. pallida, E. purpurea*), Elderberry (*Sambucus nigra*), Garlic (*Allium sativum*), Lemon balm (*Glycyrrhiza glabra*), Astragalus (*Astragalus membranaceus*), eyebright (*Euphrasia officinalis*), sage (*salvia officinalis*), yarrow (*Achillea millefolium*), nettles (*Urtica dioica*), peppermint (*menthe piperiya*), ephedra (*Ephedra sinica*), marshmallow root (*Althea officinalis*), mullein leaves or flowers (*Verbascum* spp.), plantain leaf (*Plantago lanceolata, P. major*), licorice root, thyme (*Thymus vulgaris*), boneset (*Eupatorium perfoliatum*), feverfew (*Tanacetum parthenium*), catnip (*Nepeta cataria*), yarrow (*Achillea millefolium*), elder flower (*Sambucus nigra, S. mayadenis*), ginger (*Zingiber officinale*), Ginko biloba, St. John's wort (*Hypericum perforatum* L.), zinc, lysine, foscarnet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, viracea, cytovene, famciclovir, valaciclovir, penciclovir, hexadecylosypropyl-cidofovir (HDP-CDV), nonoxynol-9, docosanol (n-docosanol, 1-docosanol, or behenyl alcohol; which is a saturated 22-carbon straight-chain alcohol), triacontanol, and salts thereof.

The antiviral agent can be present in the composition in any suitable and effective amount, provided the antiviral agent affectively inhibits or kills the desired virus. Specific exemplary amounts include, e.g., up to about 10 wt. % of the composition, up to about 5 wt. % of the composition, or up to about 1 wt. % of the composition.

Antimicrobial Agent or Preservative

The composition can optionally further include an antimicrobial agent or preservative. Suitable specific antimicrobial agents or preservatives include, e.g., quat-15, a paraben, dichlorobenzyl alcohol, ethylene diamine tetreacetic acid, formaldehyde, gum benzoin, imidazolidinyl urea, phenylmercuric acetate, poly aminopropyl biguanide, proply gallate, sorbic acid, cresol, chloroacetamide sodium benzoate, chloromethyl-methylisothiazolinone, chloromethyl-methylisothiazolon, chloromethyl-methylisothiazolinone benzalkonium chloride, an octylisothiazolinone benzimidazol-compound, chloromethyl-methylisothiazolinone octylisothiazolinone, α-phenylphenol benzisothiazolinone, o-phenylphenol benzisothiazolinone, benzisothiazolinone, an aliphatic amine of 2-thiopyridineoxide, benzoic acid, editic acid, phenolic acid, benzyl alcohol, isopropyl alcohol, benzenethonium chloride, bronopol, cetrimide, chlorohexidine, chlorobutanol, chlorocresol, phenol, phenoxyethanol, phenyl ethyl alcohol, phenylmercuric acetate, phenylmercuric borate, phenylmercuric nitrate, potassium sorbate, proplyene glycol, sodium benzoate, sodium propionate, thimerosol, and salts thereof.

The antimicrobial agent or preservative can be present in the composition in any suitable and effective amount, provided the antimicrobial agent or preservative affectively inhibits or kills the microorganism. Specific exemplary amounts include, e.g., up to about 10 wt. % of the composition, up to about 5 wt. % of the composition, or up to about 1 wt. % of the composition.

Skin Protectant

The composition can optionally further include a skin protectant. The skin protectant can act as a topical humectant, a topical conditioner, or combination thereof. Suitable specific skin protectants include, e.g., aloe, lanolin, glycerin, calamine, Vitamin E, Vitamin E acetate, Vitamin C, allantoin, aluminum hydroxide gel, bismuth subnitrate, boric acid, calamine, cocoa butter, dimethicone, kaolin, live yeast cell derivative, petrolatum, pyridoxine hydrochloride, shark liver oil, sodium bicarbonate, sulfur, tannic acid, topical starch, trolamine, white petrolatum, zinc acetate, zinc carbonate zinc oxide, zinc sulfate, and shea butter.

The skin protectant can be present in the composition in any suitable and effective amount, provided the skin protectant imparts the desired conditioning and/or moisturizing effect. Specific exemplary amounts include, e.g., up to about 10 wt. % of the composition, up to about 5 wt. % of the composition, or up to about 1 wt. % of the composition.

In various embodiments, the composition described herein can further optionally include one or more of a gelling agent (e.g., a synthetic polymer of acrylic acid), an antiseptic (e.g., at least one of a $(C_1-C_{12})$alkyl, substituted with one or more hydroxyl groups such as ethyl alcohol, isopropanol, erythritol, ethylene glycol, propylene glycol, triethylene glycol, tetraethylene glycol, and/or sorbitol), a fragrance, a coloring agent, and an essential oil.

In various embodiments, the composition described herein can effectively kill or inhibit a microorganism or pathogen, wherein the microorganism or pathogen is contacted with an effective amount of the composition, for a period of time effective to kill or inhibit the microorganism or pathogen. In specific embodiments, the contacting can occur on the surface of an animal (e.g., human or livestock).

Methods of Making the Compositions

The composition described herein can be prepared by any of the applicable techniques of chemical formulations. Many such techniques are well known in the art. For example, each of the substances of the composition can be contacted with each other, and subsequently mixed, stirred, shaken or otherwise agitated, to achieve a relatively homogeneous mixture.

Utility

The composition described herein can be used, e.g., to prevent the transmission of a communicable disease capable of being transmitted by physical contact, to reduce the number of microbes (associated with the transmission of a communicable disease) located upon a topical skin surface of an animal, and to reduce the number of microbes (associated with the transmission of a communicable disease) located upon a surface that contacts a topical skin surface of an animal. As such, while the composition described herein can be used, e.g., for the antiseptic cleansing of a topical surface of a human or other animal, the composition described herein can be used, e.g., to prevent the transmission of a communicable disease capable of being transmitted by physical contact.

The composition described herein can be applied in any suitable and effective manner. Specifically, the composition can be formulated for application to the intended surface by contacting, dipping, spraying and/or coating the composition to the intended surface.

The presently disclosed subject matter provides for a method of killing or inhibiting a microorganism or pathogen. As used herein, "killing" bacteria refers to bacteria that has been inhibited or inactivated (no longer pathogenic) or killed, as well as removed from the surface of interest (due to, for example, washing with a composition disclosed herein) and thus results in a reduced bacterial count. The method includes contacting the microorganism or pathogen with an effective amount of the composition described herein, for a period of time effective to kill or inhibit the microorganism or pathogen.

The contacting of the microorganism or pathogen with the effective amount of the composition can be in vitro or in vivo. Additionally, the contacting can occur on the surface of the animal (e.g., topical surface of a human). The compositions can be used to prevent the transmission of any one or more of the following communicable diseases or disorders:

Viral Human Infectious Diseases:
 AIDS related complex
 Chickenpox (Varicella)
 Common cold
 Dengue fever Ebola haemorrhagic fever
 Hand, foot and mouth disease
 Hepatitis A
 Hepatitis B
 Hepatitis C
 Hepatitis
 Herpes simplex
 Herpes zoster
 HPV
 Infectious mononucleosis
 Influenza (Flu)
 Lassa fever
 Marburg haemorrhagic fever
 Measles
 Mumps
 Norovirus
 Poliomyelitis
 Rabies
 Rotavirus
 Rubella
 SARS
 Smallpox (Variola)
 Viral encephalitis
 Viral gastroenteritis
 Viral meningitis.
 Viral pneumonia
Fungal Infectious Human Diseases:
 Aspergillosis
 Blastomycosis
 Candidiasis
 Coccidioidomycosis arthroconidia.
 Cryptococcosis
 Histoplasmosis
 Tinea pedis
Bacterial Infectious Human Diseases:
 Anthrax
 Bacterial meningitis
 Botulism (*Clostridium botulinum* toxicity)
 Brucellosis
 Campylobacteriosis (*Campylobacter* infection)
 Campylobacteriosis (Cat scratch disease)
 Cholera (*Vibrio cholerae* infection)
 Cholera Diphtheria.
 *Clostridium botulinum*
 *Clostridium perfringens*
 Diarrheagenic *Escherichia coli*
 *E. coli*
 Enterohemorrhagic *Escherichia coli*
 Enterotoxigenic *Escherichia coli* (ETEC)
 Epidemic Typhus
 *Escherichia coli* O157:H7 and other Shiga toxin-producing *Escherichia coli* (STEC)
 Gonorrhea
 *H. pylori*
 *Helicobacter pylori*
 Impetigo
 Legionellosis
 Leprosy (Hansen's disease)
 Leptospirosis
 Listeriosis (*Listeria* infection)
 Lyme disease.
 Melioidosis
 MRSA infection
 Nocardiosis
 Non-tuberculosis *mycobacterium* species
 Pertussis (Whooping cough)
 Plague
 Pneumococcal pneumonia
 Psittacosis
 Q fever
 Rat-bite fever
 Rocky Mountain Spotted Fever
 *Salmonella*
 *Salmonella enteritidis*
 *Salmonella typhi* (Typhoid Fever)
 Salmonellosis (*Salmonella* infection)

Scarlet fever
Shigellosis (*Shigella* infection)
*Staphylococcus* food poisoning (*Staphylococcus aureus*)
Syphilis
Trachoma
Traveler's diarrhea
Tuberculosis
Tularemia
Typhoid Fever (*Salmonella typhi* infection)
Typhus
*Vibrio parahaemolyticus*
*Vibrio vulnificus*
*Yersinia* (*Yersinia enterocolitica* infection)
*Yersinia enterocolitica*
Livestock Diseases (Sheep, Cattle, Pigs Goats, Etc):
  African horse sickness
  African swine fever
  Anaplasmosis in tick free areas
  Anthrax
  Aujeszky's disease
  Australian bat lyssavirus
  Avian Influenza
  Avian tuberculosis
  Babesiosis in tick free areas
  Bluetongue (clinical disease)
  Borna disease
  Bovine Virus Diarrhoea Type 2
  Brucellosis—(*B. abortus, B. suis, B. canis* and *B. melitensis*)
  Camelpox
  Chagas' disease (*T. cruzi*)
  Classical swine fever
  Contagious agalactia
  Contagious bovine pleuropneumonia
  Contagious caprine pleuropneumonia
  Contagious equine metritis
  Crimean Congo Haemhorragic Fever
  *Cysticercus bovis* (*Taenia saginata*)
  Devil Facial Tumour Disease
  Dourine
  Duck virus enteritis (duck plague)
  Duck virus hepatitis
  East Coast Fever (*Theileria parva*) and Mediterranean Theilerosis (*Theileria annulata*)
  Encephalitides (tick-borne)
  Enzootic bovine leucosis
  Epizootic haemhorragic disease (clinical disease)
  Epizootic lymphangitis
  Enzootic abortion of ewes
  Equine encephalomyelitis (eastern, western and Venezuelan)
  Equine encephalosis
  Equine herpes-virus 1-(abortigenic and neurological strains)
  Equine infectious anaemia
  Equine influenza
  Equine piroplasmosis (*Babesia caballi* and *Theileria equi*)
  Equine viral arteritis
  Foot and mouth disease
  Fowl typhoid
  Getah virus infection
  Glanders
  Haemorrhagic septicaemia
  Heartwater
  Hendra virus infection
  Infectious bursal disease (hypervirulent and exotic antigenic variant forms)
  Japanese encephalitis
  Jembrana disease
  Leishmaniosis of any species
  Louping ill
  Lumpy skin disease
  Maedi-visna
  Malignant catarrhal fever—(wildebeest-associated)
  Menangle virus infection
  Nairobi sheep disease
  Newcastle disease (virulent)
  Nipah virus infection
  Paratuberculosis (Johne's disease)
  Peste des petits ruminants
  Porcine enterovirus encephalomyelitis (Teschen)
  Porcine cysticercosis (*C. cellulosae*)
  Porcine myocarditis (Bungowannah virus infection)
  Porcine reproductive and respiratory syndrome
  Post-weaning multi-systemic wasting syndrome
  Potomac fever
  Pullorum disease (*Salmonella pullorum*)
  Pulmonary adenomatosis (*Jaagsiekte*)
  Rabies
  Rift Valley fever
  Rinderpest
  *Salmonella enteritidis* infection in poultry
  Salmonellosis (*S. abortus-equi*)
  Salmonellosis (*S. abortus-ovis*)
  Sheep pox and goat pox
  Sheep scab
  Surra (*Trypanosoma evansi*)
  Swine influenza
  Swine vesicular disease
  Transmissible gastroenteritis
  Transmissible spongiform encephalopathies (bovine spongiform encephalopathy, chronic wasting disease of deer, feline spongiform encephalopathy, scrapie)
  Trichinellosis
  Trypanosomosis (tsetse fly associated)
  Tuberculosis (*Mycobacterium bovis*)
  Tularaemia
  Turkey rhinotracheitis (avian metapneumovirus)
  Vesicular exanthema
  Vesicular stomatitis
  Wesselsbron disease
  West Nile virus infection—clinical In specific embodiments, the composition described herein is used for application to animals for any one or more of the following applications:

*Actinobacillus*
  *Actinomyces pyogenes.*
  *Actinomyces,*
  *Actinomycosis*—skin involvement
  Alopecia (hair loss)
  Alopecia greata
  Anaemia
  Anagen defluxation
  ANAPLASMOSIS
  Angiomatosis (Hemangioma)
  Anthrax
  Arthritis
  Atypical Myoglobinuria
  Atypical Myopathy
  Aural Plaque
  Auto-immune
  Azoturia
  Back & Neck Problems
  Baldy calf syndrome Behavioural Problems
BHV1 (IBR)— muzzle and nostrils, possibly scrotum.
BHV1 (infectious vulvovaginitis)—on genitalia
BLACKLEG
Bleeders
BLOAT
Bluetongue
Bone Cysts
Borreliosis
Bovine dermatotrophic herpesvirus (pseudo-lumpy skin)
Bovine herpes mamillitis
Bovine papular stomatitis
Bovine viral papillomatosis
Brucellosis
BSE
Buckskin Holsteins
BVD
BVDv
CALF SCOURS
Calliphorine myiasis) (Blowflies)
CANCER EYE
Cancer Colic
Chlorinated naphthalene toxicosis (X disease)
Chorioptic (Chorioptes bovis)
COCCIDIOSIS
Collagen Necrosis
Combustiones, congelationes (physical causes)
Contact dermatitis
COPD—C.O.P.D Corneal Ulcer
Cough
Cowpox
Cracked Hoof
Crib Biting—
Cribbing
Crust (dried solid accumulation, including blood, pus)
Cryptorchidism
Cryptosporidiosis
Cushings Disease
*Damalinia bovis*
Demodectic (Demodex)
Dermancentor reticulatus
Dermatitis
Dermatophilosis
Dermatophilosis (Streptothricosis)
*Dermatophilus*
*Dermatophilus* (uncommon)
Dermatosparaxis (cutaneous asthenia) (Hereditary collagen dysplasia)
Diarrhoea
DJD
DOMS
Dysautonomia Fibrous Dysplasia
Epitheliogenesis imperfecta (aplasia cutis)
Erosion (loss of superficial epidermis)
*Escherichia coli*
Excoriation (erosion and deeper ulcers—traumatic)
Exema
EXTERNAL PARASITES
Fibropapillomas
Fissure (split in superficial layers, caused by dring)
Fistulous Withers
Flies
FOOT AND MOUTH
FOOT ROT
Gangrene
Gastric Ulcer
Grass Sickness
GRASS TETANY
Greasy Heel
Guttural Pouch
Haematoma
Haematopinus eurysternus
Haemophysialis punctata
Herpes—Equine Herpes
Hives
Hoof Abscess
Hoof Quality
Hormonal Problems
Hydrotoea
Hyperkeratosis
*Hypoderma bovis, H. lineatum*
Hypodermiasis (warbles, grubs)
hypotrichosis
Hypotrichosis as BVDv-
IBR
Ichthyosis fetalis
lchtyosis congenita
Infertility
Influenza
Insolatio, siriasis (physical causes)
INTERNAL PARASITES
*Ixodes ricinis*
JOHNE'S DISEASE
Keratosis (overgrowth of dry horny keratinised epithelium)
Klebsiellosis
LEPTO
Leptospirosis
Leukotrichia and leukoderma
Lice causing skin disease (GB) Sucking:
*Linognathus vituli*
Lipomatosis
Listeriosis
Louse infestation
*Lucilia sericata*
LUMPY JAW
Lyme Disease
Lymphangitis
Lymphosarcoma
Malignant catarrhal fever
Mange (Chorioptic, Demodectic, Psoroptic)
Mastitis
Mastocytosis
Melanoma
Melanomas
Microsporum gypseum, narium, canis
Monorchidism
Moonblindness
Morrelia simplex
Mud Fever
*Musca autumnalis*
*Mycobacterium kansasii*
Myoglobinuria Navel ill
Navicular
Neoplastic skin diseases
NEOSPOROSIS
Nodular Skin Disease
OCD
Ophthalmia
Osteomyelitis
Papular stomatitis
Parakeratosis
parakeratosis (lethal trait A46)
Paralysis
Paravaccinia scrotal infections of bulls Pedal Ostitis
Periodic Ophthalmia
*Phormia terranovae*
Photosensitisation
Photosensitising diseases (types 1-4)
Pigment changes (hyper/hypo pigmentation)
PINKEYE
Polybrominated biphenyls toxicosis
Proud Flesh
Pseudocowpox
Pseudorabies (Auj)
Psoroptic (Psoroptes)
Q Fever
Quittor
Rabies
Rain Scald
RAO—Recurrent Airway Obstruction
Recurrent Uveitis—ERU Retained Testicle
Rhabdomyolysis
Ringbone—Ring Bone
Ringworm
Rug Sores
Saddle Sores
Saddling Problems
*Salmonella* dublin septicaemia (calves)
Salmonellosis
Sand Crack Sandcrack
Sarcoids
Sarcoptic (Sarcoptes)
Scale (accumulated loose fragments of superficial layers)
Scar (fibrous tissue replacing damaged skin)
Scour
Seedy Toe
Sesamoiditis
Set Fast—Setfast
Shigellosis
Solenopotes capillatus
Splints (Equine Splints)
Squamous Cell Carcinomas
Staphylococcal
Stephanofilariasis
Stomach Ulcer
Strangles
SubQ abscesses/fistulae may arise, thick honey exudate.
SubQ edema
SubQ emphysema
SubQ hematoma
Sunburn
Suspensory
Sweeney
Sweet Itch—Sweetitch
Teething
Thermal injury (sun, fire, frostbite)
Thrush
Tick-borne diseases
Tooth Abscess
TRICHOMONIASIS
Trichophytiasis (fungal)
*Trichophyton* terrucosum, metagrophytes, equinum
Tuberculosis
Ulcer—Ulceration
Ulcer (erosion penetrating basement membrane of epid)
Undescended Testicle
Urine or fecal scalding
Urticaria
Urticaria (allergic)
Urticaria, angioedema, anaphylaxis
Uveitis
Vaccination Problems Virus
Vesicular Stomatitis
VIBRIOSIS
VitC deficiency in calves
Warts
White Line Separation
Wind Sucking
Wobbler
WOODEN TONGUE
Wounds

ENUMERATED EMBODIMENTS

Specific enumerated embodiments [1] to [31] provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

[1.] A method comprising contacting a topical surface of an animal, a surface that contacts a topical surface of an animal, or a combination thereof, with an effective amount of a composition comprising:
(a) ethylhexyl sulfate of the formula

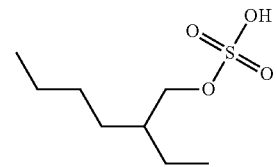

or a salt thereof;
(b) an alkylbenzenesulfonic acid of the formula

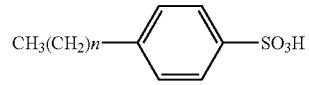

or a salt thereof, wherein n is about 5 to about 20; and
(c) an acceptable carrier.

[2.] The method of embodiment [1], wherein the ethylhexyl sulfate, or salt thereof, and the alkylbenzenesulfonic acid, or salt thereof, are present in a weight ratio of about at least about 1:1, such that based upon a weight basis, the amount of ethylhexyl sulfate, or salt thereof is at least equal to that of the alkylbenzenesulfonic acid, or salt thereof.

[3.] The method of embodiment [1], wherein the ethylhexyl sulfate, or salt thereof, and the alkylbenzenesulfonic acid, or salt thereof, are present in a weight ratio of at least about 1:2, such that based upon a weight basis, the amount of ethylhexyl sulfate, or salt thereof is at least about half that of the alkylbenzenesulfonic acid, or salt thereof.

[4.] The method of embodiment [1], wherein the ethylhexyl sulfate, or salt thereof, and the alkylbenzenesulfonic acid, or salt thereof, are present in a weight ratio of about 1:2 to about 2:1, such that based upon a weight basis, the amount of ethylhexyl sulfate, or salt thereof is from at about half to about twice that of the alkylbenzenesulfonic acid, or salt thereof.

[5.] The method of any one of embodiments [1]-[4], wherein n has an average value of about 9 to about 11.

[6.] The method of any one of embodiments [1]-[5], wherein the composition further comprises at least one of sodium hydroxide and potassium hydroxide.

[7.] The method of any one of embodiments [1]-[6], wherein the composition further comprises at least one of sodium hydroxide and potassium hydroxide, and wherein the sodium hydroxide, potassium hydroxide, or combination thereof is present in ratio of less than about 1:4, relative to the ethylhexyl sulfate, or salt thereof.

[8.] The method of any one of embodiments [1]-[7], wherein the carrier comprises water.

[9.] The method of any one of embodiments [1]-[8], wherein the composition is manufactured from:
(i) sodium 2-ethyl hexyl sulfate

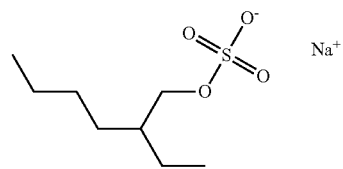

(ii) sodium chloride (NaCl);
(iii) alkylbenzene sulfonic acid

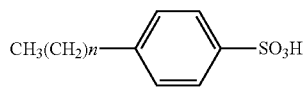

wherein n is about 10 to about 16;
(iv) benzene
(v) sulfuric acid ($H_2SO_4$);
(vi) sodium hydroxide (NaOH); and
(vii) water.

[10.] The method of any one of embodiments [1]-[9], wherein the animal is livestock.

[11.] The method of any one of embodiments [1]-[10], wherein the animal is a bovine, swine, or fowl.

[12.] The method of any one of embodiments [1]-[11], wherein the composition is a gel, lotion, cream, solution, ointment, suspension or paste.

[13.] The method of any one of embodiments [1]-[12], wherein the contacting is carried out to prevent the transmission of a communicable disease associated with at least one of a bacterium, a virus, a fungus, a mold and a mildew.

[14.] The method of any one of embodiments [1]-[12], wherein the contacting is carried out to prevent the transmission of a communicable disease associated with at least one of a gram-negative bacterium, gram-positive bacterium and an enteric bacterium.

[15.] The method of any one of embodiments [1]-[12], wherein the contacting is carried out to prevent the transmission of a communicable disease which is a viral human infectious disease.

[16.] The method of any one of embodiments [1]-[12], wherein the contacting is carried out to prevent the transmission of a communicable disease, which is a viral human infectious disease selected from the group consisting of AIDS related complex, chickenpox (varicella), common cold, dengue fever ebola haemorrhagic fever, hand, foot and mouth disease, hepatitis A, hepatitis B, hepatitis C, hepatitis, herpes simplex, herpes zoster, HPV, infectious mononucleosis, influenza (flu), lassa fever, marburg haemorrhagic fever, measles, mumps, norovirus, poliomyelitis, rabies, rotavirus, rubella, SARS, smallpox (variola), viral encephalitis, viral gastroenteritis, viral gastroenteritis, viral meningitis, and viral pneumonia.

[17.] The method of any one of embodiments [1]-[12], wherein the contacting is carried out to prevent the transmission of a communicable disease, which is a fungal infectious human disease.

[18.] The method of any one of embodiments [1]-[12], wherein the contacting is carried out to prevent the transmission of a communicable disease, which is a fungal infectious humam disease selected from the group consisting of aspergillosis, blastomycosis, candidiasis, coccidioidomycosis arthroconidia, cryptococcosis, histoplasmosis, and tinea pedis.

[19.] The method of any one of embodiments [1]-[12], wherein the contacting is carried out to prevent the transmission of a communicable disease, which is a bacterial infectious human disease.

[20.] The method of any one of embodiments [1]-[12], wherein the contacting is carried out to prevent the transmission of a communicable disease selected from the group consisting of anthrax, bacterial meningitis, botulism (*clostridium botulinum* toxicity), brucellosis, campylobacteriosis (*campylobacter* infection), campylobacteriosis (cat scratch disease), cholera (*vibrio cholerae* infection), cholera diphtheria, *clostridium botulinum*, *clostridium perfringens*, diarrheagenic *escherichia coli, E. coli*, enterohemorrhagic *escherichia coli*, enterotoxigenic *escherichia coli* (ETEC), epidemic typhus, *escherichia coli*, shiga toxin-producing *escherichia coli* (STEC), gonorrhea, *H. pylori, helicobacter pylori*, impetigo, legionellosis, leprosy (Hansen's disease), leptospirosis, listeriosis (*listeria* infection), Lymes disease, melioidosis, MRSA infection, nocardiosis, non-tuberculosis *mycobacterium*, pertussis (whooping cough), plague, pneumococcal pneumonia, psittacosis, Q fever, rat-bite fever, rocky mountain spotted fever, *salmonella, salmonella enteritidis, salmonella typhi* (typhoid fever), salmonellosis (*salmonella* infection), scarlet fever, shigellosis (*shigella* infection), *staphylococcus* food poisoning (*staphylococcus aureus*), syphilis, trachoma, traveler's diarrhea, tuberculosis, tularemia, typhoid fever, *salmonella typhi* infection, typhus, *vibrio* parahaemolyticus, *vibrio vulnificus, yersinia (yersinia enterocolitica* infection), and *yersinia enterocolitica*.

[21.] The method of any one of embodiments [1]-[12], wherein the contacting is carried out to prevent the transmission of a communicable disease, which is a livestock disease.

[22.] The method of any one of embodiments [1]-[12], wherein the contacting is carried out to prevent the transmission of a communicable disease, which is a livestock disease selected from the group consisting of African horse sickness, African swine fever, anaplasmosis in tick free areas, anthrax, Aujeszky's disease, Australian bat lyssavirus, avian influenza, avian tuberculosis, babesiosis in tick free areas, bluetongue (clinical disease), borna disease, bovine virus diarrhea type 2, brucellosis—(*B. abortus, B. suis, B. canis* and *B. melitensis*), camelpox, chagas' disease (*T. cruzi*), classical swine fever, contagious agalactia, contagious bovine pleuropneumonia, contagious caprine pleuropneumonia, contagious equine metritis, crimean congo haemhorragic fever, Cysticercus bovis (*Taenia saginata*), Devil Facial Tumour Disease, Dourine, Duck virus enteritis (duck plague), Duck virus hepatitis, East Coast Fever (*Theileria parva*) and Mediterranean Theilerosis (*Theileria annulata*), Encephalitides (tick-borne), Enzootic bovine leucosis, Epizootic haemhorragic disease (clinical disease), Epizootic lymphangitis, Enzootic abortion of ewes, Equine encephalomyelitis (eastern, western and Venezuelan), Equine encephalosis, Equine herpes-virus 1-(abortigenic and neurological strains), Equine infectious anaemia, Equine influenza, Equine piroplasmosis (*Babesia caballi* and *Theileria equi*), Equine viral arteritis, Foot and mouth disease, Fowl typhoid, Getah virus infection, Glanders, Haemorrhagic septicaemia, Heartwater, Hendra virus infection, Infectious bursal disease (hypervirulent and exotic antigenic variant forms), Japanese encephalitis, Jembrana disease, Leishmaniosis of any species, Louping ill, Lumpy skin disease, Maedi-visna, Malignant catarrhal fever—(wildebeest-associated), Menangle virus infection, Nairobi sheep disease, Newcastle disease (virulent), Nipah virus infection, Paratuberculosis (Johne's disease), Peste des petits ruminants, Porcine enterovirus encephalomyelitis (Teschen), Porcine cysticercosis (*C. cellulosae*), Porcine myocarditis (Bungowannah virus infection), Porcine reproductive and respiratory syndrome, Post-weaning multi-systemic wasting syndrome, Potomac fever, Pullorum disease (*Salmonella pullorum*), Pulmonary adenomatosis (*Jaagsiekte*), Rabies, Rift Valley fever, Rinderpest, *Salmonella enteritidis* infection in poultry, Salmonellosis (*S. abortus-equi*), Salmonellosis (*S. abortus-ovis*), Sheep pox and goat pox, Sheep scab, Surra (*Trypanosoma evansi*), Swine influenza, Swine vesicular disease, Transmissible gastroenteritis, Transmissible spongiform encephalopathies (bovine spongiform encephalopathy, chronic wasting disease of deer, feline spongiform encephalopathy, scrapie), Trichinellosis, Trypanosomosis (tsetse fly associated), Tuberculosis (*Mycobacterium bovis*), Tularaemia, Turkey rhinotracheitis (avian metapneumovirus), Vesicular exanthema, Vesicular stomatitis, Wesselsbron disease, and West Nile virus infection.

[23.] The method of any one of embodiments [1]-[22], wherein the topical surface is a hand or facial surface of the animal.

[24.] The method of any one of embodiments [1]-[23], wherein the surface that contacts the topical surface of an animal is bedding material, an animal stall, an animal living area, an animal transportation area, an animal eating area, a surface of a device that is used to contain, corral or direct the animal into a specific area, or a surface of a device that is used to prevent its free movement.

[25.] The method of any one of embodiments [1]-[24], wherein the acceptable carrier is pharmaceutically acceptable.

[26.] The method of any one of embodiments [1]-[25], wherein the acceptable carrier is veterinary acceptable.

[27.] The method of any one of embodiments [1]-[26], wherein the animal is a mammal.

[28.] The method of any one of embodiments [1]-[26], wherein the animal is a fowl or poultry.

[29.] The method of any one of embodiments [1]-[26], wherein the animal is livestock, commonly used for food, milk, hides for leather, feathers for products, or bone or bone meal for feed.

[30.] The method of any one of embodiments [1]-[29], wherein the composition is applied by spraying, rolling, dipping or brushing.

[31.] The method of any one of embodiments [1]-[30], wherein the composition further comprises a disinfectant selected from the group consisting of chlorine gas ($Cl_2$), ozone ($O_3$), lactic acid, ultraviolet light, peroxides, peracetic acid, potassium sorbate, lactic acid, and combinations thereof.

[32.] The method of any one of embodiments [1]-[31], wherein the composition further comprises an antibiotic agent.

[33.] The method of any one of embodiments [1]-[32], wherein the composition further comprises an antiviral agent.

[34.] The method of any one of embodiments [1]-[33], wherein the composition further comprises an antimicrobial agent or preservative.

[35.] The method of any one of embodiments [1]-[34], wherein the composition further comprises a skin protectant.

[36.] The method of any one of embodiments [1]-[35], wherein the composition further comprises a gelling agent.

[37.] The method of any one of embodiments [1]-[36], wherein the composition further comprises an antiseptic.

[38.] The method of any one of embodiments [1]-[37], which prevents or diminishes the occurrence of the transmission of a communicable disease in an animal, capable of being transmitted by physical contact.

[39.] The method of any one of embodiments [1]-[38], which reduces the number of microbes located upon a topical skin surface of an animal, wherein the microbes are associated with the transmission of a communicable disease.

[40.] The method of any one of embodiments [1]-[39], which washes a topical skin surface of an animal.

[41.] The method of any one of embodiments [1]-[40], which washes a surface that contacts a topical skin surface of an animal.

[42.] The method of any one of embodiments [1]-[41], which disinfects a topical skin surface of an animal.

[43.] The method of any one of embodiments [1]-[42], which disinfects a surface that contacts a topical skin surface of an animal.

Any patent, patent document, or reference disclosed herein is incorporated into reference into this disclosed subject matter and forms part of this disclosed subject matter.

What is claimed is:

1. A method of washing a topical skin surface of an animal, the method comprising contacting the surface with an effective amount of a composition comprising:
   (a) ethylhexyl sulfate of the formula

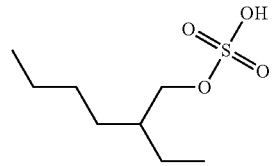

or a salt thereof;
   (b) an alkylbenzenesulfonic acid of the formula

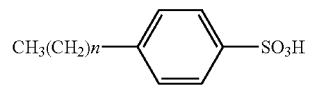

or a salt thereof, wherein n is about 5 to about 20; and
   (c) an acceptable carrier
wherein the composition is manufactured from:
   (i) sodium 2-ethyl hexyl sulfate

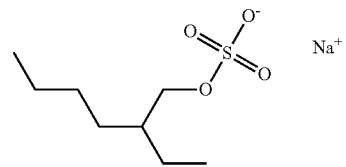

(ii) sodium chloride (NaCl);
(iii) alkylbenzene sulfonic acid

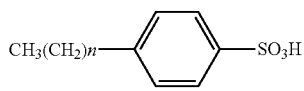

wherein n is about 10 to about 16;
(iv) benzene
(v) sulfuric acid ($H_2SO_4$);
(vi) sodium hydroxide (NaOH); and
(vii) water.

2. The method of claim 1, wherein the ethylhexyl sulfate, or salt thereof, and the alkylbenzenesulfonic acid, or salt thereof, are present in a weight ratio of about at least about 1:1, such that based upon a weight basis, the amount of ethylhexyl sulfate, or salt thereof is at least equal to that of the alkylbenzenesulfonic acid, or salt thereof.

3. The method of claim 1, wherein the ethylhexyl sulfate, or salt thereof, and the alkylbenzenesulfonic acid, or salt thereof, are present in a weight ratio of at least about 1:2, such that based upon a weight basis, the amount of ethylhexyl sulfate, or salt thereof is at least about half that of the alkylbenzenesulfonic acid, or salt thereof.

4. The method of claim 1, wherein the ethylhexyl sulfate, or salt thereof, and the alkylbenzenesulfonic acid, or salt thereof, are present in a weight ratio of about 1:2 to about 2:1, such that based upon a weight basis, the amount of ethylhexyl sulfate, or salt thereof is from at about half to about twice that of the alkylbenzenesulfonic acid, or salt thereof.

5. The method of claim 1, wherein n has an average value of about 9 to about 11.

6. The method of claim 1, wherein the composition further comprises at least one of sodium hydroxide and potassium hydroxide.

7. The method of claim 1, wherein the composition further comprises at least one of sodium hydroxide and potassium hydroxide, and wherein the sodium hydroxide, potassium hydroxide, or combination thereof is present in ratio of less than about 1:4, relative to the ethylhexyl sulfate, or salt thereof.

8. The method of claim 1, wherein the carrier comprises water.

9. The method of claim 1, wherein the animal is livestock.

10. The method of claim 1, wherein the animal is a bovine, swine, or fowl.

11. The method of claim 1, wherein the composition is a gel, lotion, cream, solution, ointment, suspension or paste.

12. The method of claim 1, wherein the topical skin surface is a hand, leg, or facial surface of the animal.

13. The method of claim 1, wherein the animal is a mammal.

14. The method of claim 1, wherein the animal is a fowl or poultry.

15. The method of claim 1, wherein the animal is livestock, commonly used for food, milk, hides for leather, feathers for products, or bone or bone meal for feed.

16. The method of claim 1, wherein the composition is applied by spraying, rolling, dipping or brushing.

17. The method of claim 1, wherein the composition optionally comprises a disinfectant selected from the group consisting of chlorine gas ($Cl_2$), ozone ($O_3$), lactic acid, ultraviolet light, peroxides, peracetic acid, potassium sorbate, and combinations thereof.

18. A method of washing a surface that contacts a topical skin surface of an animal, the method comprising contacting the surface with an effective amount of a composition comprising:
(a) ethylhexyl sulfate of the formula

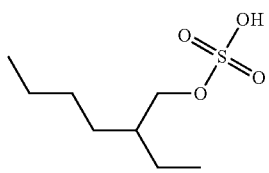

or a salt thereof;
(b) an alkylbenzenesulfonic acid of the formula

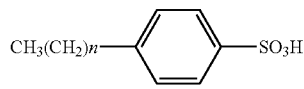

or a salt thereof, wherein n is about 5 to about 20; and
(c) an acceptable carrier
wherein the composition is manufactured from:
(i) sodium 2-ethyl hexyl sulfate

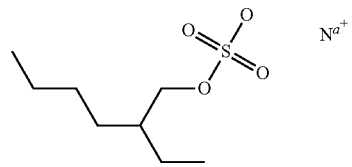

(ii) sodium chloride (NaCl);
(iii) alkylbenzene sulfonic acid

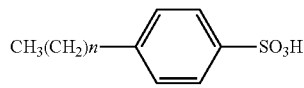

wherein n is about 10 to about 16;
(iv) benzene
(v) sulfuric acid ($H_2SO_4$);
(vi) sodium hydroxide (NaOH); and
(vii) water.

19. The method of claim 18, wherein the surface that contacts a topical skin surface of an animal is bedding material, an animal stall, an animal living area, an animal transportation area, an animal eating area, a surface of a device that is used to contain, corral or direct the animal into a specific area, or a surface of a device that is used to prevent its free movement.

* * * * *